United States Patent
Kondo et al.

(10) Patent No.: US 8,790,712 B2
(45) Date of Patent: Jul. 29, 2014

(54) CONSTITUTIONAL FUNCTION-IMPROVING AGENTS

(75) Inventors: Masao Kondo, Kita-ku (JP); Naomi Aiba, Ota-ku (JP); Setsuko Miyanari, Minato-ku (JP); Tohru Tanaka, Minato-ku (JP); Takaya Suzuki, Minato-ku (JP); Masahiro Ishizuka, Minato-ku (JP)

(73) Assignees: Cosmo Oil Co., Ltd., Tokyo (JP); SBI Pharmaceuticals Co., Ltd., Tokyo (JP)

( * ) Notice: Subject to any disclaimer, the term of this patent is extended or adjusted under 35 U.S.C. 154(b) by 0 days.

(21) Appl. No.: 11/661,688

(22) PCT Filed: Aug. 26, 2005

(86) PCT No.: PCT/JP2005/015560
§ 371 (c)(1),
(2), (4) Date: Mar. 2, 2007

(87) PCT Pub. No.: WO2006/025286
PCT Pub. Date: Mar. 9, 2006

(65) Prior Publication Data
US 2008/0026075 A1    Jan. 31, 2008

(30) Foreign Application Priority Data

Sep. 2, 2004 (JP) ................. 2004-255575
Sep. 2, 2004 (JP) ................. 2004-255576
Sep. 2, 2004 (JP) ................. 2004-255577
Jul. 28, 2005 (JP) ................. 2005-218435
Jul. 28, 2005 (JP) ................. 2005-218436

(51) Int. Cl.
*A61K 33/34* (2006.01)

(52) U.S. Cl.
USPC ........... 424/630; 424/639; 424/641; 424/646; 514/561

(58) Field of Classification Search
CPC ............. A61K 31/197; A61K 41/0061; A61K 2300/00; A61K 33/24
USPC ............... 424/630, 639, 641, 646; 514/561
See application file for complete search history.

(56) References Cited

U.S. PATENT DOCUMENTS 5,234,940 A    8/1993    Kennedy et al.
5,368,841 A    11/1994   Trauner et al.
(Continued)

FOREIGN PATENT DOCUMENTS

EP    1413303 A1    4/2004
GB    1068478 A     5/1967
(Continued)

OTHER PUBLICATIONS

Chandra, Proceedings of the Nutrition society,1993, 52, pp. 77-84.*
(Continued)

*Primary Examiner* — Savitha Rao
*Assistant Examiner* — Angela Brown-Pettigrew
(74) *Attorney, Agent, or Firm* — Sughrue Mion, PLLC

(57) ABSTRACT

The present invention is drawn to a method of inducing thymocyte proliferation in a vertebrate animal with an impaired immune system comprising administering δ-aminolevulinic acid or a salt thereof every day in succession. The method further comprises administering at least one mineral.

15 Claims, 2 Drawing Sheets

THYMUS OF UN-ADMINISTERED GROUP

THYMUS OF ALA-ADMINISTERED GROUP

(56) References Cited

U.S. PATENT DOCUMENTS

| | | | |
|---|---|---|---|
| 5,955,490 A * | 9/1999 | Kennedy et al. | 514/561 |
| 2001/0053796 A1* | 12/2001 | Kim et al. | 514/561 |
| 2004/0234555 A1* | 11/2004 | Oshida et al. | 424/230.1 |

FOREIGN PATENT DOCUMENTS

| | | | |
|---|---|---|---|
| JP | 04-502019 A | | 4/1992 |
| JP | 9-505822 A | | 6/1997 |
| JP | 9-505823 A | | 6/1997 |
| JP | 10-215811 A | | 8/1998 |
| JP | 2000-083932 A | | 3/2000 |
| JP | 2001-512471 A | | 8/2001 |
| JP | 2002-535364 A | | 10/2002 |
| JP | 2003-040770 A | | 2/2003 |
| JP | 2003-277284 A | | 10/2003 |
| JP | 2004-224899 A | | 8/2004 |
| KR | 2003097164 | * | 12/2003 |
| WO | 9417797 A1 | | 8/1994 |
| WO | 02/49635 A2 | | 6/2002 |

OTHER PUBLICATIONS

Cunningham-Rundles, American Journal of Clinical Nutrition, 35, May 1982, pp. 1202-1210.*
Hotta et al., Plant Growth Regulators, vol. 22, pp. 109-114, 199.*
Siegel et al CA Cancer J Clin 2012;62:220-241.*
Sowers et al Hypertension. 2001;37:1053-1059.*
Demasi M., Costa C.A., Pascual C. et al., Oxidative tissue response promoted by 5-aminolevulinic acid promptly induces the increase of plasma antioxidant capacity, Free Radical Research, 1997, vol. 26, No. 3, pp. 235 to 243.
Monteiro H.P., Bechara E.J., Abdalla D.S., Free radicals involvement in neurological porphyrias and lead poisoning, Molecular and Cellular Biochemistry, 1991, vol. 103, No. 1, pp. 73 to 83.
Chinese Office Action dated Jan. 23, 2009.
Notice Requesting Submission of Opinion in counterpart Korean Application No. 10-2007-7007605, dated Jan. 14, 2010.
Office Action, dated Dec. 10, 2012, issued by the Canadian Intellectual Property Office in counterpart Canadian Application No. 2,752,569.
Communication dated Nov. 24, 2011, issued by the State Intellectual Propert Office of P.R. China in counterpart Chinese Application No. 201010150020.9.
Database WPI Week 200430 (2003), Thomson Scientific, London, GB; AN 2004-326013, XP002689564, 1 page total.
Extended European Search Report dated Jan. 11, 2013 issued by the European Patent Office in counterpart European Patent Application No. 05774552.3.
Di Jian, et al., "Blood Doping and Erythropoiesis-Stimulating Agents (ESA)-Misunderstanding in athletic enhancement", Journal of Xi'an Institute of Physical Education, Jun. 30, 1998, pp. 88-91, vol. 15, No. 2, Abstract.
Communication from the State Intellectual Property Office of P.R. China dated Feb. 17, 2011 in a counterpart application No. 201010150020.9.
Japanese Office Action, dated Oct. 19, 2010 issued in Application No. 2004-255576.
Japanese Office Action, dated Oct. 19, 2010, issued in Application No. 2005-218435.
Japanese Office Action, dated Oct. 19, 2010, issued in Application No. 2005-218436.
Search Report dated Mar. 28, 2014 issued by the European Patent Office in counterpart European Patent Application No. 14153023.8.
Meneguello M. O. et al; Effect of arginine, ornithine and citrulline supplementation upon performance and metabolism of trained rats; Cell Biochemistry and Function; XP009116476; vol. 21; No. 1; Mar. 1, 2003; pp. 85-91.
Cutinelli L et al; "Protection by ornithine-aspartate of the effects of physical exercise"; CAPLUS; XP003011544; 1970.

* cited by examiner

THYMUS OF ALA-ADMINISTERED GROUP

THYMUS OF UN-ADMINISTERED GROUP

CONSTITUTIONAL FUNCTION-IMPROVING AGENTS

TECHNICAL FIELD

The present invention relates to health function-improving agents. More specifically, it relates to an immunological function-improving agent capable of increasing resistance to infection, aging and the like, and an antioxidation function-improving agent, a exercise function-improving agent, a liver function-improving agent and the like which are useful in preventing or treating life-style diseases such as arteriosclerosis, cancer and diabetes mellitus, abnormal pigmentation such as spots and freckles, inflammation of the skin, senescence of the skin and the like.

BACKGROUND ART

Immune function is a basic function possessed by animals for keeping life, by selectively excluding such a case that a pathogen or the like which is disadvantageous to the existing of themselves invades into the body or a cancer or the like is generated therein. The immunological function is realized by mutual cooperation and regulation of various lymphocytes, macrophages, leukocytes and the like distributed mainly in thymus and also in spleen, lymph node, bone marrow and the like.

A drug which improves the immunological function is useful as a preventive or therapeutic agent for cancers, a therapeutic agent for various autoimmune diseases and the like, as well as a medicine or food for increasing resistance to various infections and the like. It is the that, among a large number of amino acids, glutamine and arginine have the action to improve immunological function (Patent Reference 1).

In addition, it is broadly known that active oxygens typified by superoxide radical and hydrogen peroxide have cytotoxicity and are the cause of cancer, rheumatism, spots, wrinkles and the like. Also, it is known that LDL which carries cholesterol is changed to oxidized LDL by active oxygen, and the changed oxidized LDL becomes a cause of arteriosclerosis.

Thus, since it is said that a pharmaceutical agent having an antioxidation action is useful in preventing or treating life-style diseases such as arteriosclerosis, cancer and diabetes mellitus, abnormal pigmentation such as spots and freckles, inflammation of the skin, senescence of the skin and the like, various antioxidation action components have been found. For example, it is known that the antioxidation action can be found in natural substances such as vitamin E and vitamin C, synthetics such as BHT (3,5-tert-butyl-4-hydroxytoluene) and BHA (2,3-tert-butyl-hydroxyanisole), crude drugs and the like (Patent Reference 2).

On the other hand, health function of human and animals is reduced by fatigue, disease, pregnancy, aging, nutritional disorder or poor nutrition. This fatigue includes physical fatigue and mental fatigue, and not only physical fatigue but also mental fatigue is greatly concerned in the fatigue of the moderns.

Among these, a complex carbohydrate of saccharides and starch and the like are used as a nourishment effective for the physical fatigue. Also, as medicaments, a vitamin B group such as vitamin $B_1$, vitamin $B_2$ and nicotinic acid, melatonin, vitamin C, vitamin E, magnesium and the like are used.

In addition, it has been reported recently that amino acids of a specific composition containing essential amino acids and nonessential amino acids have an effect to improve exercise function at the time of fatigue (Patent Reference 3). The essential amino acids include valine, leucine, isoleucine, lysine, threonine, methionine and the like, and the nonessential amino acids include arginine, glutamine, proline and the like.

Patent Reference 1: JP-A-2002-3372
Patent Reference 2: JP-A-10-139678
Patent Reference 3: JP-A-9-249556

DISCLOSURE OF THE INVENTION

Problems to be Solved by the Invention

However, among the amino acids considered to have the immunological function-improving action, glutamine has a problem in that it has low solubility and is unstable, so that it is degraded into glutamic acid and ammonia in the body, and it is known that arginine has side effects of causing chapped skin, thickening of the skin, swelling of joints and malformation of bones, so that it is necessary to take care about its intake.

In addition, there are problems in that vitamin E and vitamin C are safe as natural substances, but their effect as an antioxidation agent are not sufficient, and BHT and BHA have a possible danger of having carcinogenic property, and the like. Regarding those derived from crude drugs, their effect as an antioxidation agent are not sufficient, too.

Accordingly, an object of the present invention is to provide health function-improving agents such as an antioxidation function-improving agent, a exercise function-improving agent and a liver function-improving agent which can be taken for a prolonged period of time.

Means for Solving the Problems

Thus, the present inventors have examined on the pharmacological actions of various amino acids and found that δ-amino acids typified by 5-aminolevulinic acid have excellent immunological function-improving action, by increasing weight of the thymus which is important as a tissue that carries immunological function, and by promoting growth of thymus cell and cytotoxic T cell. Also, the present inventors have found that δ-amino acids typified by 5-aminolevulinic acid can improve the activity of superoxide dismutase (SOD) or glutathione peroxidase (GPx) known as an antioxidation enzyme, and therefore have excellent antioxidation function improving action. In addition, the present inventors have found that δ-amino acids typified by 5-aminolevulinic acid have significantly increasing health function and liver function improving action, in adult animals, and the present invention has been accomplished based on these findings.

That is, the present invention relates to the following (1) to (19).

(1) A compound selected from a δ-amino acid, a derivative thereof and a salt thereof, which is useful as a health function-improving agent.

(2) Use of a δ-amino acid, a derivative thereof or a salt thereof as a health function-improving agent.

(3) Use of a δ-amino acid, a derivative thereof or a salt thereof for the manufacture of a health function-improving agent.

(4) Use of a functional food or drink comprising, as an effective ingredient, a δ-amino acid, a derivative thereof or a salt thereof as a health function-improving agent.

(5) The compound or use according to any one of (1) to (4), wherein the health function-improving agent is an immunological function-improving agent.

(6) The compound or use according to (5), wherein the immunological function-improving agent is a thymus cell growth agent.

(7) The compound or use according to any one of (1) to (4), wherein the health function-improving agent is an antioxidation function-improving agent.

(8) The compound or use according to any one of (1) to (4), wherein the health function-improving agent is a exercise function-improving agent.

(9) The compound or use according to any one of (1) to (4), wherein the health function-improving agent is a liver function-improving agent.

(10) The compound or use according to any one of (1) to (9), wherein the δ-amino acid, the derivative thereof or the salt thereof is a compound represented by the following formula (I)

$$R^1-NHCH_2COCH_2CH_2COOR^2 \quad (I)$$

wherein $R^1$ represents a hydrogen atom or an acyl group; and $R^2$ represents a hydrogen atom or a hydrocarbon group which may have a substituent(s), or a salt thereof.

(11) The compound or use according to (10), wherein the hydrocarbon group which may have a substituent(s) is a hydrocarbon group substituted with at least one selected from the group consisting of a hydroxyl group, an alkoxy group, an acyloxy group, an alkoxycarbonyloxy group, an amino group, an aryl group, an oxo group, a fluoro group, a chloro group and a nitro group.

(12) The compound or use according to any one of (1) to (11), wherein the health function-improving agent comprises a mineral.

(13) The compound or use according to any one of (5), (6) and (10) to (12), wherein the immunological function-improving agent comprises at least one mineral selected from the group consisting of iron, copper, selenium, zinc and manganese.

(14) The compound or use according to any one of (7) and (10) to (12), wherein the antioxidation function-improving agent comprises at least one mineral selected from the group consisting of copper, zinc manganese and selenium.

(15) The compound or use according to any one of (8) and (10) to (12), wherein the exercise function-improving agent comprises at least one mineral selected from the group consisting of iron, magnesium, manganese and zinc.

(16) The compound or use according to any one of (9) to (12), wherein the liver function-improving agent comprises at least one mineral selected from the group consisting of iron, magnesium, manganese and zinc.

(17) The compound or use according to any one of (1) to (3) and (5) to (16), wherein the health function-improving agent is an agent for oral, injection, ophthalmic, suppository, fomentation, patch, aerosol, tubal or enteral ingestion.

(18) The compound or use according to any one of (1) to (3) and (5) to (16), wherein the health function-improving agent is a food or drink.

(19) The compound or use according to any one of (1) to (18), wherein the health function-improving agent comprises a δ-amino acid, a derivative thereof or a salt thereof such that it is ingested in an amount of from 0.001 to 1000 mg per body weight per day.

Effects of the Invention

According to the present invention, health function of an animal whose health function was reduced, such as an animal including human whose health function was reduced accompanied by aging, can be improved. More specifically, according to the present invention, immunological function of an animal whose health function was reduced, such as an animal including human whose immunological function was reduced accompanied by aging, can be improved, so that resistance to an infection and the like can be increased. Also, according to the present invention, antioxidation function of an animal whose antioxidation function was reduced, such as an animal including human whose antioxidation function was reduced accompanied by aging, can be improved, so that life-style diseases such as arteriosclerosis, cancer and diabetes mellitus, abnormal pigmentation such as spots and freckles, inflammation of the skin, senescence of the skin and the like can be prevented or improved. Also, according to the present invention, exercise function of an animal whose exercise function was reduced, such as an animal including human whose exercise function was reduced accompanied by aging, can be improved. In addition, according to the present invention, liver function of an animal whose liver function was reduced, such as an animal including human whose liver function was reduced accompanied by aging, can be improved.

BEST MODE FOR CARRYING OUT THE INVENTION

Figure 1:
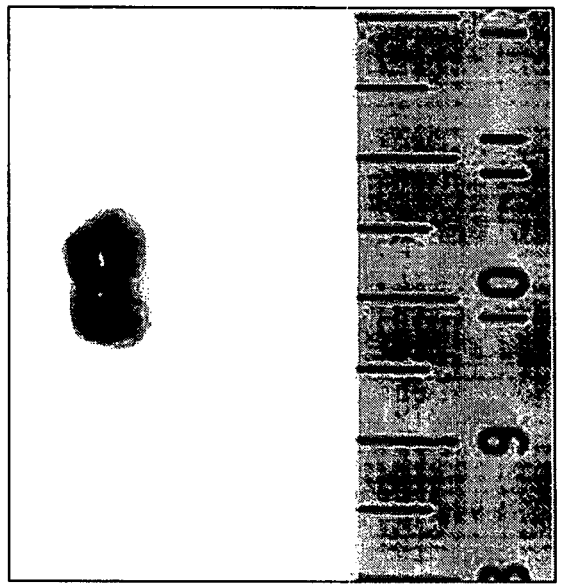
FIG. 1 is a view showing thymus photographs of 5-aminolevulinic acid un-administered group and administered group.
Figure 1:
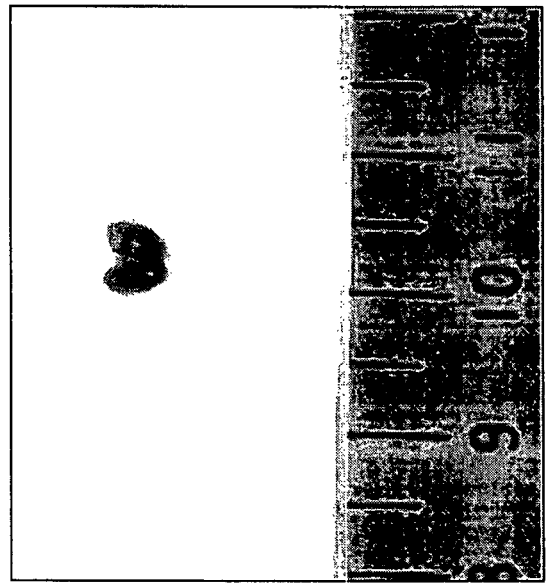

An effective component of the health function-improving agent of the present invention is a δ-amino acid, a derivative thereof or a salt thereof (hereinafter also referred to as "δ-amino acids"). Examples of the δ-amino acids include a 5-aminolevulinic acid represented by the following formula (I):

$$R^1-NHCH_2COCH_2CH_2COOR^2 \quad (I)$$

(in the formula, $R^1$ represents a hydrogen atom or an acyl group; and $R^2$ represents hydrogen atom or a hydrocarbon group which may have a substituent(s)), a derivative thereof and a salt thereof (hereinafter also referred to as "5-aminolevulinic acids").

It is known that δ-amino acids such as 5-aminolevulinic acids are useful as a photosensitizer in the photodynamic therapy (JP-T-2004-505105), a plant growth regulator (JP-A-07-53487), a herbicide (JP-A-05-117110), a therapy of infection of fishes with pathogenic microorganisms and parasites (JP-A-2001-316255), a hog growth accelerator (JP-A-2003-40770) and the like.

Examples of the acyl group represented by $R^1$ in formula (I) include an alkanoyl group having from 1 to 24 carbon atoms, an aromatic acyl group, a benzyloxycarbonyl group and the like. Specific examples include an acyl group, an acetyl group, a n-propanoyl group, a n-butanoyl group, a n-pentanoyl group, a n-hexanoyl group, a n-nonanoyl group, a benzyloxycarbonyl group and the like. Among these, an alkanoyl group having from 1 to 6 carbon atoms is more preferable.

In addition, examples of the hydrocarbon group which may have a substituent(s) represented by $R^2$ include a hydrocarbon group which may have at least one substituent selected from hydroxy, alkoxy, acyloxy, alkoxycarbonyloxy, amino, aryl, oxo, fluoro, chloro and nitro and the like. In this case, an alkyl group, an alkenyl group, an aralkyl group or an aryl group is preferable as the hydrocarbon group. In this case, the alkyl group include a straight, branched or cyclic alkyl group, and an alkyl group having from 1 to 40, preferably from 1 to 18, particularly from 1 to 7, carbon atoms is preferable. The alkenyl group is a straight, branched or cyclic alkyl group, and an alkenyl group having from 2 to 40, preferably from 2 to 18, carbon atoms is preferable. The aralkyl group includes one containing an aryl group having from 6 to 20 carbon atoms and an alkyl group having from 1 to 6 carbon atoms. In addition, the aryl group includes an aryl group having from 6 to 20 carbon atoms.

The alkoxy group is preferably an alkoxy group having from 1 to 18 carbon atoms, and more preferably an alkoxy group having from 1 to 7 carbon atoms. The acyloxy group is preferably an alkanoyloxy group having from 1 to 18 carbon atoms, and more preferably an alkanoyloxy group having from 2 to 8 carbon atoms. The alkoxycarbonyloxy group is preferably a $C_{1-18}$ alkoxy-carbonyloxy group, and more preferably a $C_{1-7}$ alkoxy-carbonyloxy group.

Examples of the preferred alkyl group having from 1 to 18 carbon atoms include a methyl group, an ethyl group, a n-propyl group, an isopropyl group, a n-butyl group, an isobutyl group, a tert-butyl group, a n-pentyl group, an isopentyl group, a neopentyl group, a tert-pentyl group, a 2-methylbutyl group, a n-hexyl group, an isohexyl group, a 3-methylpentyl group, an ethylbutyl group, a n-heptyl group, a 2-methylhexyl group, a n-octyl group, an isooctyl group, a tert-octyl group, a 2-ethylhexyl group, a 3-methylheptyl group, a n-nonyl group, an isononyl group, a 1-methyloctyl group, an ethylheptyl group, a n-decyl group, a 1-methylnonyl group, a n-undecyl group, a 1,1-dimethylnonyl group, a n-dodecyl group, a n-tridecyl group, a n-tetradecyl group, a n-pentadecyl group, a n-hexadecyl group, a n-heptadecyl group, a n-octadecyl group and the like.

Examples of the more preferred alkyl group having from 1 to 7 carbon atoms include a methyl group, an ethyl group, a n-propyl group, an isopropyl group, a n-butyl group, an isobutyl group, a tert-butyl group, a n-pentyl group, an isopentyl group, a neopentyl group, a tert-pentyl group, a 2-methylbutyl group, a n-hexyl group, an isohexyl group, a 3-methylpentyl group, an ethylbutyl group, a n-heptyl group and a 2-methylhexyl group.

Examples of the hydroxyl-substituted alkyl group having from 1 to 18 carbon atoms include 2-hydroxyethyl, 3-hydroxypropyl, 4-hydroxybutyl, 5-hydroxypentyl, 6-hydroxyhexyl and the like.

Examples of the alkoxy-substituted alkyl group having from 1 to 18 carbon atoms include $C_{1-7}$ alkoxy-$C_{1-18}$ alkyl groups such as 2-methoxyethyl, 2-ethoxyethyl, 3-methoxypropyl, 3-ethoxypropyl, 4-methoxybutyl, 4-ethoxybutyl and 2-(2-methoxyethyl)ethyl.

Examples of the acyloxy-substituted alkyl group include a $C_{2-7}$ alkanoyloxy-$C_{1-18}$ alkyl group. Examples of the alkoxycarbonyloxy-substituted alkyl group include a $C_{1-18}$ alkoxy-carbonyloxy-$C_{1-8}$ alkyl group.

Examples of the amino group-substituted alkyl group include an amino-$C_{1-18}$ alkyl group.

Examples of the alkenyl group having from 2 to 18 carbon atoms include a vinyl group, an allyl group, an isopropenyl group, a 2-butenyl group, a 2-methylallyl group, a 1,1-dimethylallyl group, a 3-methyl-2-butenyl group, a 3-methyl-3-butenyl group, a 4-pentenyl group, a hexenyl group, an octenyl group, a nonenyl group, a decenyl group, a cyclopropenyl group, a cyclobutenyl group, a cyclopentenyl group, a cyclohexenyl group, a cycloheptenyl group, a cyclooctenyl group, a 4-methylcyclohexenyl group, a 4-ethylcyclohexenyl group, a 2-cyclopentenylethyl group, a cyclohexenylmethyl group, a cycloheptenylmethyl group, a 2-cyclobutenylethyl group, a 2-cyclooctenylethyl group, a 3-(4-methylcyclohexenyl)propyl group, a 4-cyclopropenylbutyl group, a 5-(4-ethylcyclohexenyl)pentyl group, an oleyl group, a vaccenyl group, a linoleyl group, a linolenyl group, a trans-9-octadecenyl group, a 9E,12E-octadecadienyl group, a 9E, 12E, 15E-octadecatrienyl group and the like.

The aralkyl group having from 7 to 26 carbon atoms is preferably one containing an alkyl group having from 1 to 6 carbon atoms and an aryl group having from 6 to 20 carbon atoms. Examples of the alkyl group having from 1 to 6 carbon atoms include a methyl group, an ethyl group, a n-propyl group, an isopropyl group, a n-butyl group, an isobutyl group, a tert-butyl group, a n-pentyl group, a n-hexyl group, a cyclopropyl group, a cyclobutyl group, a cyclohexyl group and the like, and examples of the aryl group having from 6 to 20 carbon atoms include a phenyl group, a naphthyl group and the like. The aralkyl group having from 7 to 26 carbon atoms is preferably a benzyl group, a phenethyl group or a 9-fluorenylmethyl group, and more preferably a benzyl group or a fluorenylmethyl group. The aryl group in the aralkyl group may be substituted with 1 to 3 substituents, for example, the above-described alkyl group having from 1 to 6 carbon atoms, an alkoxy group having from 1 to 6 carbon atoms such as a methoxy group, an ethoxy group, a n-propoxy group, a n-butoxy group, an isobutoxy group and a tert-butoxy group, a hydroxyl group, an amino group, a nitro group, a cyano group, a halogen atom such as fluorine, chlorine, bromine and iodine, a carboxyl group, and the like.

Examples of the aryl group having from 6 to 20 carbon atoms include a phenyl group, a naphthyl group and the like, which may be substituted with 1 to 3 substituents, including an alkyl group having from 1 to 6 carbon atoms such as a methyl group, an ethyl group, a n-propyl group, an isopropyl group, a n-butyl group, an isobutyl group, a tert-butyl group, a n-pentyl group, a n-hexyl group, a cyclopropyl group, a cyclobutyl group, a cyclohexyl group or the like, an alkoxy group having from 1 to 6 carbon atoms such as a methoxy group, an ethoxy group, a n-propoxy group, a n-butoxy group, an isobutoxy group and a tert-butoxy group, a hydroxyl group, an amino group, a nitro group, a cyano group, a halogen atom such as fluorine, chlorine, bromine and iodine, a carboxyl group and the like. In this connection, although the above-described $R^1$ and $R^2$ represent a substituent of the amino group and the carboxylic acid group, respectively, these exemplified substituents are substituents of not only 5-aminolevulinic acids but also δ-amino acids.

Examples of the salt of a δ-amino acid or a derivative thereof include acid addition salts such as hydrochloride, hydrobromide, hydroiodide, phosphate, methyl phosphate, ethyl phosphate, phosphite, hypophosphite, nitrate, sulfate, acetate, propionate, toluenesulfonate, succinate, oxalate, lactate, tartarate, glycolate, methanesulfonate, butyrate, valerate, citrate, fumarate, maleate and malate, metal salts such as a sodium salt and a calcium salt, an ammonium salt, an alkyl ammonium salt, and the like. In this connection, these salts are used as a solution or powder when used.

The above δ-amino acid, derivative thereof or salt thereof may form a hydrate or solvate, and can be used alone or as an optional combination of two or more.

The δ-amino acids can be produced by any one of the methods of chemical synthesis, microbial production and enzymatic production. In addition, among the above-described δ-amino acids, 5-aminolevulinic acids can be produced in accordance with the methods described in JP-A-48-92328, JP-A-62-111954, JP-A-2-76841, JP-A-6-172281, JP-A-7-188133, JP-A-11-42083 and the like. The δ-amino acids produced in the above manner and the chemical reaction solutions or fermentation solutions before their purification can be used as such without carrying out separation and purification, with the proviso that they do not contain harmful substances. In addition, commercial items and the like can also be used.

Specific examples of the health function-improving agent of the present invention include an immunological function-improving agent, an antioxidation function-improving agent, a exercise function-improving agent, a liver function-improving agent and the like.

Specifically, as is described later in Examples, the above-described δ-amino acids have the action to improve lowered immunological function, by increasing thymus weight of a mouse whose immunological function was lowered due to advanced age. Thus, the above-described δ-amino acids are useful as an immune improving agent for animals including human, and particularly useful as an immunological function-improving agent for animals including human having lowered immunological function due to advanced age.

As described above, the present invention relates to an immunological function-improving agent, but in a narrow sense, the immunological function-improving agent of the present invention is a thymus cell growth agent which is capable of growing thymus cells in a mouse by orally administering it to the mouse as is shown later in Examples. Also, in a more narrow sense, this is a cellular T cell growth agent which rendered possible growth of cellular T cells in a mouse by orally administering it to the mouse as is shown later in Examples. Such a function of the δ-amino acid in in vivo body has not been predicted and therefore is a useful invention in the coming aging society.

In addition, as is described later in Examples, the above-described δ-amino acids have the action to improve lowered antioxidation function, by particularly reinforcing SOD activity or GPx activity of a mouse whose antioxidation function was lowered due to advanced age. Thus, the above-described δ-amino acids are useful as an antioxidation improving agent for animals including human, and particularly useful as an antioxidation function-improving agent for animals including human having lowered antioxidation function due to advanced age, and also as an anti-aging improving agent.

Furthermore, as is described later in Examples, the above-described δ-amino acids has the action to improve lowered health function, or exercise function in a narrow sense, by increasing active movement of a mouse whose health function was lowered due to advanced age, or by accelerating weight gain.

In addition, as is described later in Examples, the above-described δ-amino acids has the action to decrease γ-GTP value of a mouse by orally administering it to the mouse.

Accordingly, the above-described δ-amino acids are useful as health function-improving agents for animals including human, such as an immunological function-improving agent, an antioxidation function-improving agent, a exercise function-improving agent and a liver function-improving agent, and are particularly useful as a health function-improving agent for animals including human whose health function was lowered due to aging.

Also, regarding the health function-improving agent of the present invention, its effect can be further improved when a mineral is contained therein or simultaneously ingested therewith. Examples of the mineral include iron, zinc, copper, phosphorus, calcium, magnesium, potassium, selenium, chrome, manganese, iodine, boron, silicon, vanadium, molybdenum, cobalt and the like. When the health function-improving agent is used as an immunological function-improving agent, particularly preferable mineral is iron, copper, selenium, zinc or manganese. When it is used as an antioxidation function-improving agent, particularly preferable minerals is copper, zinc, manganese or selenium. When it is used as a exercise function-improving agent or a liver function-improving agent, particularly preferable mineral is iron, magnesium, manganese or zinc. These minerals may be used alone or by a combination of two or more. Any chemical property of the minerals can be used, so long as it is not injurious to organisms.

If necessary, other nutrients, antioxidants and the like can be added to the health function-improving agent of the present invention. Examples of the nutrients, essential amino acids, nonessential amino acids, vitamins, internal factors such as taurine, coenzyme Q10 and α lipoic acid, herbs, protein, various enzymes and the like. Examples of the antioxidants include polyphenols such as ubiquinone and ferulic acid, flavonoids such as N-acetylcysteine, cysteine, catechol, tocopherol, catechin and quercetin, and the like.

The health function-improving agent of the present invention can also be used by allowing carrier such as an excipient to adsorb a powder of δ-amino acids, an aqueous solution prepared by dissolving a powder of δ-amino acids in water, or a δ-amino acids-containing fermentation solution produced by the above-described method. The kind of the carrier may be a general substance, and examples include crystalline cellulose, gelatin, starch, dextrin, oil cake, baker's yeast, beer yeast, sake yeast, wine yeast, skim milk powder, lactose, animal and plant fats and oils, anhydrous calcium phosphate, calcium carbonate, magnesium stearate, aluminum magnesium silicate, aluminum magnesium metasilicate and the like.

The dosage forms of the health function-improving agent of the present invention includes injections, tablets, capsules, fine subtilaes, syrups, suppositories, ophthalmic solutions, fomentations, patches, aerosols and the like. They can be produced in accordance with the usual methods by optionally using pharmaceutically acceptable carriers such as a solvent, a dispersion medium, an extender and an excipient, and the like. In addition, these may be ingested as a form of food and drink.

When the health function-improving agent of the present invention is prepared as an aqueous solution, and when the δ-amino acids are 5-aminolevulinic acids, it is necessary to take such an attention that the aqueous solution does not become alkaline for the purpose of preventing degradation of the active ingredient, 5-aminolevulinic acid. When it becomes alkaline, degradation of the active ingredient can be prevented by removing oxygen.

The health function-improving agent of the present invention may be sufficient enough when the health function can be improved by ingesting this agent, so that the method for using this agent has no limitation, but preferred conditions are shown in the following.

Although the animal as an object of the health function-improving agent of the present invention is not particularly limited, vertebral animals such as mammals, reptiles, birds, amphibia and fishes are preferable. Examples include human, cattle, pig, sheep, goat, mouse, rat, rabbit, dog, cat, domestic fowl, quail, fresh water fishes such as rainbow trout, carp, eel and mountain trout, sea fishes such as silver salmon, yellow tail, red sea bream, mackerel and tuna, and organisms for display such as tropical fishes and reptiles, and the like.

Use of the agent as an immunological function-improving agent is possible at any growth stage of the animal, but preferably, after ceasing of the increase of weight of the thymus tissue is preferable. It is preferable to use the immunological function-improving agent at or after 15 years old, particularly preferably at or after 30 years old, in the case of human.

Use of the agent as an antioxidation function-improving agent is possible at any growth stage of the animal, but preferably, after reduction of the antioxidation function, such as SOD activity or GPx activity, is preferable. It is preferable to use the antioxidation function-improving agent at or after 15 years old, particularly preferably at or after 30 years old, in the case of human.

Use of the health function-improving agent as a exercise function-improving agent or liver function-improving agent is possible at any growth stage of the animal, but it is preferably at or after 15 years old, particularly preferably at or after 30 years old, in the case of human.

Although the method for ingesting the health function-improving agent of the present invention is not particularly limited, examples include oral, injection, ophthalmic, suppository, fomentation, patch, aerosol, tubal and enteral ingestion, and oral ingestion is particularly preferable.

Although the agent shows sufficient effect by one ingestion, it can be ingested two or more times for further improving the effect. The two or more times of ingestion is effective regarding the effect per agent to be ingested, and it is the efficient using method to ingest in small potions every day.

Ingesting amount of the agent per once per 1 kg of the animal to be treated is preferably from 0.001 mg to 1000 mg, more preferably from 0.001 mg to 100 mg, and most preferably from 0.001 mg to 50 mg. As the ingesting amount of the agent, a larger amount is required when the growth is vigorous or the ingestion frequency is less. The ingestion exceeding a proper range is not preferable, because it is uneconomical and has a possibility of causing sunlight damage.

In addition, when minerals are jointly used, they may be used simultaneously or used separately. Kind of the mineral to be used, a using method thereof and a using amount thereof may be the same as those of the minerals generally put on the market. The using amount is, for example, from 1 to 45 mg, preferably from 5 to 20 mg, per day per male adult in the case of iron. In the case of copper, it is from 0.5 to 10 mg, preferably from 1 to 5 mg, per day per male adult. In the case of zinc, it is from 1 to 40 mg, preferably from 5 to 20 mg. In the case of manganese, it is from 0.1 to 11 mg, preferably from 2 to 8 mg. In the case of selenium, it is from 10 to 250 μg, preferably from 20 to 100 μg. In the case of magnesium, it is from 50 mg to 700 mg, preferably from 100 to 500 mg.

EXAMPLE 1

The present invention is described below in detail based on Examples, but the present invention is not limited thereto. Also, % means % by weight unless otherwise indicated.

EXAMPLE 1

Mice (35 to 45 weeks old, BALB/cAJc1) preliminary raised for 1 week were injected with 10 mg of 5-aminolevulinic acid (hereinafter referred to as "ALA") hydrochloride per kg mouse body weight once a day for 7 days continuously. ALA hydrochloride was adjusted to a concentration of 0.5 g/ml with distilled water and orally administered to the mice. After the test, each mouse was sacrificed and the weight of its thymus was measured. The test was carried out using 5 mice per 1 plot, and their values were shown by average value. The results are shown in Table 1. In the plot treated with ALA hydrochloride, the thymus weight which is greatly concerned in the immunological function was significantly increased in both cases of males and females, and it was confirmed that the effect was markedly expressed particularly in males.

TABLE 1

|  | Thymus (g) |
| --- | --- |
| Untreated ♂ | 0.021 |
| ALA-treated ♂ | 0.035 |
| Untreated ♀ | 0.035 |
| ALA-treated ♀ | 0.038 |

EXAMPLE 2

Mice (35 to 45 weeks old, BALB/cAJc1) preliminary raised for 1 week were injected with 10 mg of ALA hydrochloride per 1 kg mouse body weight once a day for 7 days continuously. ALA hydrochloride was adjusted to a concentration of 0.5 g/ml with distilled water and orally administered to the mice. After the test, each mouse was sacrificed and the weight of its thymus and the number of cells were measured. In addition, a subset test of lymphocytes was carried out using the obtained cells. The results are shown in Table 2 and Table 3. The test was carried out using 5 mice per 1 plot, and their values were shown by average value. In the plot treated with ALA hydrochloride, the thymus weight which is greatly concerned in the immunological function was increased in both cases of males and females, and the number of cells was also increased significantly in comparison with the untreated plot (Table 2). Also, since the cell of CD4-CD8+ was increased in the ALA-treated plot based on the subset test, it was confirmed that the cytotoxic T cell increases after its future differentiation, so that its immunological function improving ability was shown (Table 3). In addition, photographs of the thymus of untreated plot (unadministered group) and the thymus of ALA-treated plot (ALA-treated group) are shown in FIG. 1.

TABLE 2

|  | Thymus (g) | The number of cells |
| --- | --- | --- |
| Untreated ♂ | 0.021 | $9.6 \times 10^6$ |
| ALA-treated ♂ | 0.034 | $22.0 \times 10^6$ |
| Untreated ♀ | 0.026 | $40.0 \times 10^6$ |
| ALA-treated ♀ | 0.044 | $49.9 \times 10^6$ |

TABLE 3

|  | CD4-CD8+ (%) |
| --- | --- |
| Untreated ♂ | 4.36 |
| ALA-treated ♂ | 5.55 |
| Untreated ♀ | 3.00 |
| ALA-treated ♀ | 3.25 |

EXAMPLE 3

Mice (35 to 45 weeks old, BALB/cAJc1) preliminary raised for 1 week were injected with 10 mg of ALA hydrochloride per 1 kg mouse body weight once a day for 7 days continuously. ALA hydrochloride was adjusted to a concentration of 0.5 g/ml with distilled water and orally administered to the mice. After the test, each mouse was sacrificed and the thymus of mouse was collected to measure superoxide dismutase (SOD) activity of its tissue. To the collected thymus, 1.0 ml of 0.25 M sucrose solution was added, and the mixture homogenized and then centrifuged at 10,000 G for 10 minutes, and the resulting supernatant solution was used as the enzyme solution. The measurement was carried out using an emission reagent for antioxidant ability measurement, MPEC (2-methyl-6-p-methoxyphenylethynylimidazopyrazinone) (manufactured by Atto Corp.). That is, 250 µl of a reaction solution containing 125 µl of 0.1 M potassium phosphate buffer (pH 7.5), 10 µl of the enzyme liquid, 60 µl of 0.1 unit/ml xanthine oxidase, 45 µl of distilled water and 10 µl of 0.3 mM MPEC was dispensed into Luminescencer-PSN (manufactured by Atto Corp.), 50 µl of 0.72 mM hypoxanthine (pH 7.5) was added for emission. For the calculation of emission inhibition ratio, the buffer was used instead of the enzyme liquid. For the calculation, a calibration curve was prepared using standard SOD, and the concentration calculation was carried out using this.

In addition, glutathione peroxidase (GPx) activity was also measured. After 0.6 ml of a reaction mixture (containing 0.05 M K-phosphate buffer (pH 7.0), 1 mM NaN$_3$, 1 mM EDTA and 4 mM GSH) was kept at 37° C., 0.1 ml of 2 mM H$_2$O$_2$ and 50 µl of the enzyme solution were added into the cell of a spectrophotometer and the total volume was adjusted to 1 ml, and the scanning was carried out directly by the spectrophotometer for 2 minutes (20 mm/min) at a wavelength of 340 nm (OD at 340 nm).

The calculation was carried out by the following formula using the molecular extinction coefficient of NADPH of a=6.3 cm$^2$/µmole, by calculating the slope of straight line ΔOD (ΔOD=Δcm (quantity of change of y axis)×OD Max/full cm) from the chart.

GPx activity=$V$/adv×Δ$OD$/Δ$t$ ($V$ is a volume of the reaction solution, d=light path=1 cm, v=amount of the enzyme, Δt=quantity of change of time min)

The test was carried out using 5 male and 5 female mice, a total of 10 animals, for each plot, and the values were shown by average value. The results are shown in Table 4. It was confirmed that the SOD activity or GPx activity is improved in both cases of male and female in the ALA-treated plot.

TABLE 4

|  | SOD activity (U/ml) | Total SOD activity (U/organ) | GPx activity (U/ml) |
|---|---|---|---|
| Untreated plot ♂ | 9.2 | 9.39 | 0.37 |
| ALA plot ♂ | 20.2 | 20.95 | 0.61 |
| Untreated plot ♀ | 25.9 | 26.81 | 0.59 |
| ALA plot ♀ | 30.7 | 31.84 | 0.67 |

EXAMPLE 4

Mice (35 to 45 weeks old, BALB/cAJc1) preliminary raised for 1 week were injected with 10 mg of ALA hydrochloride per 1 kg mouse body weight once a day for 7 days continuously. ALA hydrochloride was adjusted to a concentration of 0.5 g/ml with distilled water and orally administered to the mice. After the test, the mouse was put into a cage of 20 cm×20 cm in floor area, and its migration distance was measured for 5 minutes. The test was carried out using 5 male and 5 female mice, a total of 10 animals, for each plot, and the values were shown by average value. The results are shown in Table 5. It was confirmed that the migration distance is long and the capacity for locomotion is improved in both cases of male and female in the ALA-treated plot. In addition, symptoms such as abnormal stimulation and action were not observed on the ALA-treated mice during the test.

TABLE 5

|  | Exercise quantity (m) |
|---|---|
| Untreated plot ♂ | 15 |
| ALA plot ♂ | 41 |
| Untreated plot ♀ | 9 |
| ALA plot ♀ | 25.5 |

EXAMPLE 5

Mice (35 to 45 weeks old, BALB/cAJc1) preliminary raised for 1 week were injected with 10 mg of ALA hydrochloride per 1 kg mouse body weight once a day for 7 days continuously. ALA hydrochloride was adjusted to a concentration of 0.5 g/ml with distilled water and orally administered to the mice. After the test, each mouse was sacrificed to collect mouse blood, and ALA dehydrase (ALAD) activity (the activity of ALA in which it is dimerized and thereby forms porphobilinogen (hereinafter referred to as "PBG") as one molecule pyrrole substance) and porphobilinogen deaminase (PBGD) activity (the activity to convert from PBG to hydroxymethylbilane) per 1 ml of the blood were measured. The pathway in which ALA forms PBG and the pathway in which PBG is converted into hydroxymethylbilane are a part of the important pathway of heme synthesis. To 0.02 ml of heparin-treated mouse whole blood, 0.33 ml of distilled water was added, the mixture was adjusted to a total volume of 0.5 ml by adding thereto 0.05 ml of 0.5 M Na-phosphate buffer (pH 6.4), 0.05 ml of 0.1 M DTT (containing 1 mM ZnSO$_4$) and 0.05 ml of 50 mM ALA hydrochloride and was kept at 37° C. for 30 minutes, the reaction was stopped by adding 0.5 ml of 1 M trichloroacetic acid, and then Ehrlich reagent was added to a supernatant after centrifugation at 3000 rpm in the same volume, and precisely 10 minutes thereafter, absorbance at 553 nm, which is a characteristic absorbance of the compound formed by the reaction of Ehrlich reagent with PBG, was measured (OD) using a spectrophotometer.

Calculation was carried out in the following manner using the molar extinction coefficient 61000 of the reaction product PBG obtained by the ALAD activity. The reaction time of 0 minute was used as the blank (OD$_o$).

$ALAD$ activity = $1M \times (OD - OD_0)/61000 \times 2/1000 \times$ $1/0.02 \times 1$ mol $PBG/HT/h$ = $1.639 \times (OD - OD_0)/Ht\mu$mol $PBG$/ml $RBC/h$ (Ht represents hematocrit value, RBC represents erythrocyte and h represents time)

In addition, the RBGD activity was measured in the following manner. To 0.02 ml of heparin-treated mouse whole blood, 0.38 ml of distilled water was added thereto, 0.05 ml of 0.6 mM PBG (containing 0.38 M Na-phosphate buffer (pH 7.8)) was further added thereto, and then the mixture was kept at 37° C. for 30 minutes. The reaction was stopped by adding 0.05 ml of 5 M trichloroacetic acid (containing 0.8% iodine), and then the supernatant after centrifugation at 3000 rpm for 5 minutes was directly subjected to the measurement of fluorescence intensity at an excitation wavelength of 405 nm and a fluorescence wavelength of 597 nm, using a spectrofluorometer.

The calculation was carried out by proportional calculation using uroporphyrin I (URO) type isomer which is a standard substance of the oxidation type uroporphyrinogen I.

That is,

FU (fluorescence intensity of Em=597 nm)
=139 when the standard substance 0.536 nmol URO/ml accordingly, $$RBGD \text{ activity} = 0.536/139 \times 0.5/0.02 \times 2 \times FU/Ht/h$$

$$= 0.192 \times FU/Ht \, n\text{mol } URO/\text{ml } RBC/h$$

(Ht represents hematocrit value, RBC represents erythrocyte and h represents time)

The test was carried out using 5 male mice per plot, and the values were shown by average value. The results are shown in Table 6. It was confirmed that the ALAD activity and PBGD activity are improved in the ALA-treated plot.

TABLE 6

|  | ALAD activity (μmol PBG/ml RBC/h) | PBGD activity (nmol URO/ml RBC/h) |
|---|---|---|
| Untreated plot ♂ | 1.28 | 55.71 |
| ALA plot ♂ | 1.76 | 67.36 |

As described in the above, it was found that the activities of the heme synthesis pathway (ALAD activity and PBGD activity) which constitutes heme proteins as important factors of the respiratory electron transport system are improved when ALA is treated. Thus, it was considered that the citric acid cycle (TCA cycle) which carries out energy metabolism in the animal body was activated by the activation of this pathway, and the exercise function was improved thereby.

EXAMPLE 6

Mice (35 to 45 weeks old, BALB/cAJc1) preliminary raised for 1 week were injected with 10 mg of ALA hydrochloride per 1 kg mouse body weight once a day for 7 days continuously. ALA hydrochloride was adjusted to a concentration of 0.5 g/ml with distilled water and orally administered to the mice. The mouse was put into a rotary exercise quantity measuring device (rotating basket: 200 mm in diameter×50 mm in width, raising basket: W 90 mm×D 220 mm×H 90 mm, manufactured by Shinano Seisakusho) and the number of rotation within 16 hours was measured before and after the test. The test was carried out using 1 mouse per 1 rotary exercise quantity measuring device, and carried out on female mice using untreated 5 animals and ALA-treated 5 animals as 1 plot, and the values were shown by the average value. The results are shown in Table 7. It was confirmed that the rotation quantity was large and the exercise capacity was improved in the plot treated with ALA.

TABLE 7

|  | Before the test | | After the test | | Increasing ratio before and after the test (%) |
|---|---|---|---|---|---|
|  | Number of rotation | Distance (m) | Number of rotation | Distance (m) |  |
| Untreated ♂ | 10505 | 6597 | 11829 | 7429 | 113 |
| ALA-treated ♂ | 11297 | 7095 | 14155 | 8889 | 125 |

EXAMPLE 7

A total of 120 animals (60 animals for each of male and female) of about 4 weeks old of ddY-N mouse produced by Nippon Ikagaku Dobutsu Shizai Kenkyusho Co., Ltd. was purchased and subjected to 1 week of medical inspection to confirm that their healthy state is normal, and then used in the test. The test plots were set to a total of 4 plots of a control plot in which distilled water for injection is administered into the stomach using a stomach tube at a ratio of 10 ml per 1 kg body weight of the mouse to be tested for 28 continuous days, and 3 test plots in which ALA hydrochloride is administered in the same manner at respective ratios of 5 mg, 10 mg and 25 mg per 1 kg body weight of the mouse to be tested. The mice to be tested were divided into 12 groups, 1 group including 5 males or females, in such a manner that average body weight of each group became almost uniform, and 3 groups of males or females were allotted to each plot and raised for 28 days. The mice to be tested were raised by each group using a series of five stainless steel cages arranged in a raising room set to a room temperature of 23.0±2.0° C. and an irradiation time of 12 hours/day. Body weight gain was calculated by measuring individual body weight at intervals of 1 week from the start of the test.

Figure 2:
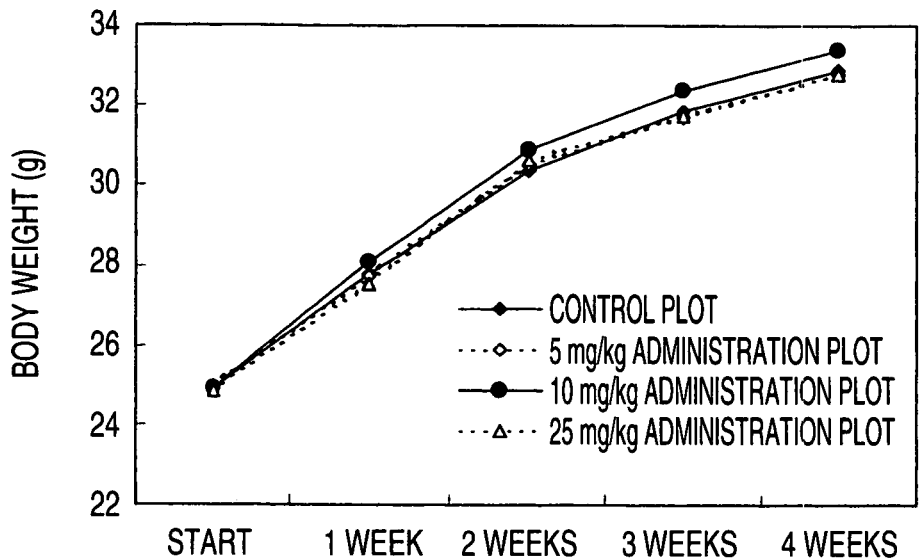
FIG. 2 is a graph showing growth curve of a mouse.

As a result, as shown by the growth curves (averages of males and females, FIG. 2) during the test period, the 10 mg/kg administration plot showed superior growth than other 3 plots, and when combined with the results of Example 6, exercise function was improved and weight gain effect was also found, so that it was found that this is useful as a health function-improving agent.

In this connection, abnormal health state was not fund in the ALA-treated groups.

EXAMPLE 8

LW·D piglets produced on the same day at a swinery were purchased 3 times, each time for 14 animals (each 7 animals of castrates and females), and subjected to preliminary raising for 9 to 12 days to confirm that their healthy state is normal, and then 12 animals (each 6 animals of castrates and females) were selected for each time and used in the test. The test plots were set to a total of 3 plots of a control plot in which a control feed (Table 8) without adding ALA hydrochloride is provided, and 2 test plots in which 10 ppm or 50 ppm of ALA hydrochloride is added to the feed and provided. The piglets to be tested were divided into 3 groups, each group including 4 animals (each 2 animals of castrates and females), in such a manner that distribution of body weight became almost uniform, and 1 groups was allotted to each plot and raised for 6 weeks. The swinery used in the test was an open type swinery in which a pig chamber of 1.8×2.7 m concrete floor was arranged in a row of 14 chambers, and group feeding was carried out using adjoining 3 pig chambers for each block. Rice straws were used as the bedding. A warm-keeping box was arranged in each pig chamber for 3 weeks after start of the test. The feed and drinking water were constantly provided. Body weight gain was calculated by measuring individual body weight at intervals of 1 week from the start of the test. The results are shown in Table 8.

Figure 3:
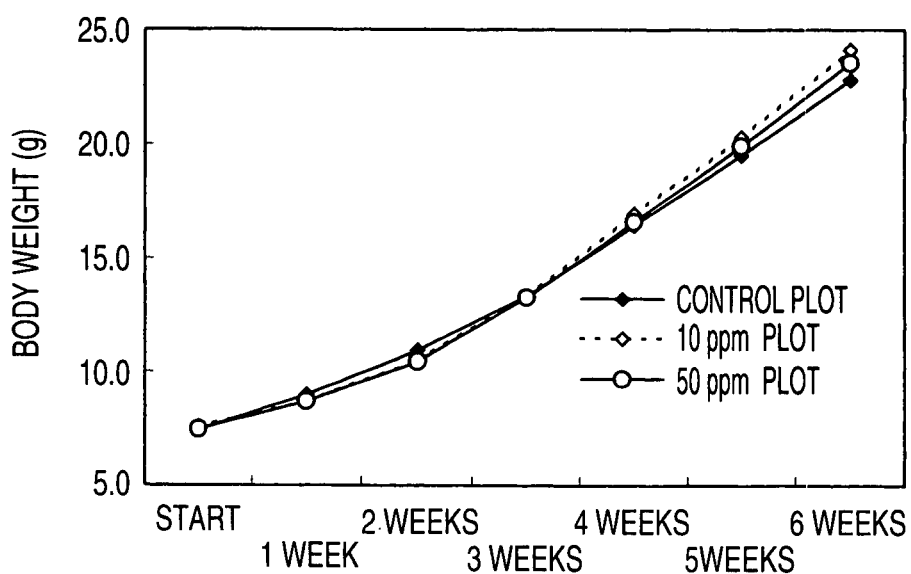
FIG. 3 is a graph showing growth curve of a raised hog.

As a result, as shown by the growth curves (average of castrated or female animals, FIG. 3) during the test period, the 10 ppm and 50 ppm addition plots showed superior growth than the control plot, and when combined with the results of Example 6, exercise function was improved and weight gain effect was also found, so that it was found that this is useful as a health function-improving agent.

In this connection, abnormal health state was not fund in the ALA-treated groups.

TABLE 8

Mixing ratio of control feed (%)

| Materials | Mixing ratio | Materials | Mixing ratio |
|---|---|---|---|
| Corn | 50.60 | Calcium sec. phosphate | 0.05 |
| Wheat flour | 19.00 | Sodium chloride | 0.20 |
| Bean cake | 5.00 | Vitamin B group [1] | 0.10 |
| Fish meal | 1.50 | Vitamin ADE [2] | 0.10 |
| Skim milk powder | 5.00 | Trace minerals [3] | 0.10 |
| Conc. soybean protein | 9.00 | L-lysine hydrochloride | 0.46 |
| Glucose | 5.00 | L-tryptophan | 0.04 |
| Powdered oils and fats | 2.00 | L-threonine | 0.10 |
| Calcium carbonate | 0.75 | | |
| | | Total | 100.00 |
| Composition [4] | | | |
| CP (%) | 18.7 | Leu | 1.86 |
| DE (Mcal/kg) | 3.49 | Effective Lys | 0.99 |
| Ca (%) | 0.69 | Effective Met + Cys | 0.68 |
| NpP (%) | 0.37 | Phe + Tyr | 1.43 |
| Arg | 0.93 | Effective Thr | 0.65 |
| His | 0.48 | Trp | 0.22 |
| Ile | 0.64 | Val | 0.83 |

Note [1]
In 1 kg; thiamin nitrate 1.0, riboflavin 7.0, pyridoxine hydrochloride 0.5, nicotinic acid amide 6.0, calcium D-pantothenate 10.9, choline chloride 57.6
Note [2]
In 1 g, vitamin A 10,000 IU, vitamin D 32,000 IU, dl-α-tocopherol acetate 10 mg
Note [3]
In 1 kg, Mn 50 g, Fe 50 g, Cu 10 g, Zn 60 g, I 1 g
Note [4]
Component composition is calculated value

EXAMPLE 9

A total of 300 chicks, 150 chicks for females and males respectively, of broiler primary chicks (Chunky) were purchased. After the purchase, chicks having abnormality (weakness or dwarf) were excluded, and the rest were equipped with wing belts for individual identification and their body weights were individually measured. As shown in Table 10, females or males were divided into 3 groups (45 chicks or more per 1 group) based on their body weights, and allotted to 3 groups, each for 15 chicks, at random in each group. Using 15 female or male chicks (30 chicks in total) as 1 group, they were put into a Chick Gird arranged in a closed type barn, and warmed by arranging an infrared ray lamp for animal use. The Chick Gird was expanded along with the growth of chicks. The feed and drinking water were constantly provided. The test groups were set to a total of 3 groups containing a control group in which a control feed (a standard testing feed SDB No. 1 was used from the neonatal to 3 weeks old, or a standard testing feed SDB No. 2 from 3 weeks old to 7 weeks old, (both manufactured by Nippon Formula Feed Mfg Co., Ltd., Table 9) without adding ALA hydrochloride is provided, and 2 test groups of ALA-10 ppm treated group and ALA-50 ppm treated group in which 10 ppm or 50 ppm of ALA hydrochloride is added to the feed and provided, and 3 repetition plots were arranged for each group. The number of chicks to be tested in each test group was as shown in Table 10. The test period was set to 7 weeks (7 weeks old) from the neonatal (start of the added feed provision), and total body weight of females or males was measured for each repetition plot at the time of the neonatal and at intervals of 1 week thereafter. In addition, about 2 ml of blood was collected from a brachial vein (basilic vein) of each of 18 chicks (3 female or male chicks/repetition) of each group at 3 weeks old and 7 weeks old, and about 1.5 ml thereof was subjected to a coagulation preventing treatment using heparin-lithium salt and then the blood plasma was separated to inspect the items of LDH, GOT (AST), γ-GTP, ALP, total protein, albumin, globulin, total cholesterol, triglyceride, glucose, uric acid, total bilirubin, uric acid, creatinine, calcium and inorganic phosphorus. The results are shown in Tables 11 and 12. As a result, regarding the body weight (average of females or males) during the test period, difference in the body weight of the neonatal to 3 weeks old was not found between the test groups as shown in Table 11, but the body weight of in and after 3 weeks old in the ALA-10 ppm treated group and ALA-50 ppm treated group became larger than the control group. In addition, as a result of the blood test, as shown in Table 12, it was found that γ-GTP (gamma glutamyl transpeptidase) was decreased in the ALA-10 ppm treated group and ALA-50 ppm treated group in comparison with the control group, so that it was found that ALA has an effect to improve liver function and therefore is useful as a health function-improving agent.

In this connection, also in the ALA-treated groups, no abnormality was found in the general conditions during the test period, and an abnormality considered to be due to its addition was not found regarding the raising ratio and pathologic autopsy findings.

TABLE 9

Materials and general components of tested feed

| Components | SDB No. 1 (neonatal to 3 weeks old) | SDB No. 2 (3 to 7 weeks old) |
|---|---|---|
| Crude protein (%) | 23.8 | 20.0 |
| Crude fat (%) | 5.8 | 6.8 |
| Crude fiber (%) | 2.5 | 2.6 |
| Crude ash (%) | 5.2 | 5.0 |
| Calcium (%) | 1.04 | 1.02 |
| Phosphorus (%) | 0.73 | 0.73 |
| Total energy (Mcal/kg) | 4.14 | 4.13 |
| Metabolizable energy (Mcal/kg) | 3.07 | 3.16 |

Materials: corn, Hokuyo meal, soybean oil cake, wheat flour, alfalfa meal, vitamins, minerals, amino acids

TABLE 10

Setting of test groups

| Test groups | The number of chicks tested |
|---|---|
| Control group | 30 chicks (15 female or male chicks) × 3 repetition plots, 90 chicks in total |
| ALA-10 ppm group | 30 chicks (15 female or male chicks) × 3 repetition plots, 90 chicks in total |
| ALA-50 ppm group | 30 chicks (15 female or male chicks) × 3 repetition plots, 90 chicks in total |
| Total | 270 chicks |

TABLE 11

Results of body weight measurement

| | Growth (g) | | | | | | | |
|---|---|---|---|---|---|---|---|---|
| | Neonatal | 1 week | 2 week | 3 week | 4 week | 5 week | 6 week | 7 week |
| Control group | 37.8 | 169.2 | 439.6 | 802.6 | 1367.4 | 2008.1 | 2703.5 | 3301.7 |
| ALA-10 ppm group | 37.8 | 166.3 | 442.0 | 817.2 | 1402.7 | 2063.9 | 2736.4 | 3420.9 |
| ALA-50 ppm group | 37.7 | 169.1 | 436.8 | 807.7 | 1400.8 | 2036.7 | 2731.5 | 3403.3 |

TABLE 12

Results of γ-GTP measurement

| | γ-GTP (IU/l) | |
|---|---|---|
| | 3 weeks old | 7 weeks old |
| Control group | 30.7 | 33.3 |
| ALA-10 ppm group | 29.7 | 29.7 |
| ALA-50 ppm group | 30.0 | 32.7 |

While the invention has been described in detail and with reference to specific embodiments thereof, it will be apparent to one skilled in the art that various changes and modifications can be made therein without departing from the spirit and scope of the invention.

This application is based on a Japanese patent application filed on Sep. 2, 2004 (Japanese Patent Application No. 2004-255575), a Japanese patent application filed on Sep. 2, 2004 (Japanese Patent Application No. 2004-255576), a Japanese patent application filed on Sep. 2, 2004 (Japanese Patent Application No. 2004-255577), a Japanese patent application filed on Jul. 28, 2005 (Japanese Patent Application No. 2005-218435) and a Japanese patent application filed on Jul. 28, 2005 (Japanese Patent Application No. 2005-218436), the entire contents thereof being thereby incorporated by reference. The entire contents of the cited references are incorporated by reference.

INDUSTRIAL APPLICABILITY

According to the present invention, health function of an animal whose health function was reduced, such as an animal including human whose health function was reduced accompanied by aging, can be improved.

The invention claimed is:

1. A method of inducing thymocyte proliferation in a vertebrate animal with an impaired immune system comprising:
    identifying a vertebrate animal in need of increasing a weight of the vertebrate animal's thymus, wherein said vertebrate animal is a mammal or a bird, and
    administering a dose of δ-aminolevulinic acid or a salt thereof every day in succession to maintain a constant effective amount of δ-aminolevulinic acid or a salt thereof sufficient to increase the weight of the vertebrate animal's thymus.

2. The method according to claim 1, wherein δ-aminolevulinic acid or a salt thereof is a thymus cell growth agent.

3. The method according to claim 1, wherein δ-aminolevulinic acid or salt thereof is co-administered with at least one mineral.

4. The method according to claim 3, wherein the one mineral selected from the group consisting of iron, copper, selenium, zinc and manganese.

5. The method according to claim 2, wherein δ-aminolevulinic acid or a salt thereof is administered orally, by injection, ophthalmically, as a suppository, by fomentation, in a patch, as an aerosol, via tube or by enteral ingestion.

6. The method according to claim 1, wherein the δ-aminolevulinic acid or a salt thereof is added to a food or drink.

7. The method according to claim 1, wherein the δ-aminolevulinic acid or a salt thereof is ingested in an amount of from 0.001 to 1000 mg per body weight per day.

8. The method according to claim 1, wherein the vertebrate animal is a human.

9. The method according to claim 8, wherein the human is at least 15 years old.

10. The method according to claim 1, wherein said effective amount of δ-aminolevulinic acid or a salt thereof induces thymocyte proliferation.

11. The method according to claim 1, wherein said period of time sufficient to increase the weight of the mammal's thymus is at least about one week.

12. The method according to claim 1, wherein said period of time sufficient to increase the weight of the mammal's thymus is at least about four weeks.

13. A method of inducing thymocyte proliferation in a human with an impaired immune system comprising:
    identifying a human in need of thymocyte proliferation, wherein said human is 15 years of age or older, and
    administering continuously a dose of δ-aminolevulinic acid or a salt thereof every day to maintain a constant effective amount of δ-aminolevulinic acid or a salt thereof for a period of time sufficient to increase the weight of the human's thymus,
    wherein said δ-aminolevulinic acid or a salt thereof is administered orally or by injection.

14. A method of inducing thymocyte proliferation in a vertebrate animal with an impaired immune system consisting of:
    identifying a vertebrate animal in need of thymocyte proliferation, wherein said animal is a mammal or a bird, and
    administering continuously a dose of δ-aminolevulinic acid or a salt thereof every day to maintain a constant effective amount of δ-aminolevulinic acid or a salt thereof for a period of time sufficient to increase the weight of the animal's thymus.

15. A method of inducing thymocyte proliferation in a vertebrate animal with an impaired immune system comprising:
    identifying a vertebrate animal in need of thymocyte proliferation, wherein said animal is a mammal or a bird, but not including a pig, and
    administering continuously a dose of δ-aminolevulinic acid or a salt thereof every day to maintain a constant effective amount of δ-aminolevulinic acid or a salt thereof for a period of time sufficient to increase the weight of the animal's thymus.

* * * * *